United States Patent [19]

Iwanaga et al.

[11] Patent Number: 6,127,301
[45] Date of Patent: Oct. 3, 2000

[54] CATALYST SYSTEM AND METHOD FOR REACTION OF OLEFIN

[75] Inventors: Kiyoshi Iwanaga; Mitsuhisa Tamura, both of Chiba, Japan

[73] Assignee: Sumitomo Chemical Company, Limited, Osaka, Japan

[21] Appl. No.: 08/884,124

[22] Filed: Jun. 27, 1997

[30] Foreign Application Priority Data

Jun. 28, 1996 [JP] Japan .................................. 8-169933
Apr. 9, 1997 [JP] Japan .................................. 9-090780

[51] Int. Cl.$^7$ .............................. B01J 31/00; B01J 21/08; C07C 2/02; C08F 4/44
[52] U.S. Cl. ........................... 502/119; 502/123; 502/162; 502/164; 502/167; 502/171; 502/200; 502/228; 502/232; 502/238; 585/522; 585/523; 585/525; 585/527; 585/529; 585/530; 585/532; 526/128; 526/139; 526/141; 526/142
[58] Field of Search .................................. 502/119, 123, 502/162, 164, 167, 171, 200, 228, 232, 238; 585/522, 523, 525, 527, 529, 530, 532; 526/128, 139, 141, 142

[56] References Cited

U.S. PATENT DOCUMENTS

| | | | |
|---|---|---|---|
| Re. 31,099 | 12/1982 | Scata et al. ........................... | 526/128 |
| 3,173,901 | 3/1965 | Newberg et al. ..................... | 526/128 |
| 3,269,996 | 8/1966 | Langer, Jr. ............................ | 526/139 |
| 3,691,095 | 9/1972 | Kroll et al. ........................... | 502/102 |
| 4,290,918 | 9/1981 | Bayer et al. .......................... | 502/159 |
| 4,777,315 | 10/1988 | Levine et al. ........................ | 585/512 |
| 5,151,399 | 9/1992 | Job ....................................... | 502/125 |
| 5,185,410 | 2/1993 | Job ....................................... | 502/124 |
| 5,225,502 | 7/1993 | Sato et al. ............................ | 502/125 |
| 5,227,355 | 7/1993 | Seppala et al. ....................... | 502/125 |
| 5,229,344 | 7/1993 | Job ....................................... | 502/120 |
| 5,345,023 | 9/1994 | Chauvin et al. ...................... | 585/527 |
| 5,371,157 | 12/1994 | Job ....................................... | 502/125 |
| 5,523,507 | 6/1996 | Reagen et al. ........................ | 585/513 |
| 5,731,487 | 3/1998 | Tamura et al. ....................... | 585/513 |
| 5,814,715 | 9/1998 | Chen et al. ........................... | 526/348.6 |
| 5,856,610 | 1/1999 | Tamura et al. ....................... | 585/517 |

FOREIGN PATENT DOCUMENTS

| | | |
|---|---|---|
| 0 237 079 | 9/1987 | European Pat. Off. .......... C07C 2/32 |
| 0 614 865 | 9/1994 | European Pat. Off. .......... C07C 2/30 |
| 0668105 | 8/1995 | European Pat. Off. . |
| 6-239920 | 8/1994 | Japan . |
| 9-176228 | 7/1997 | Japan . |
| WO9623010 | 8/1996 | WIPO . |

*Primary Examiner*—Mark L. Bell
*Assistant Examiner*—Patricia L. Hailey
*Attorney, Agent, or Firm*—Sughrue, Mion, Zinn, Macpeak & Seas, PLLC

[57] ABSTRACT

The present invention provides a novel catalyst system which can be preferably used in the trimerization, oligomerization reaction or polymerization reaction of an olefin, and a method for the trimerization, oligomerization or polymerization reaction of an olefin, which comprises using the catalyst system. A catalyst system obtained by contacting the following components (A) to (C):

(A) a chromium compound, (B) an imine compound, and (C) a metal alkyl compound, and a method for the trimerization, oligomerization or polymerization reaction of an olefin, which comprises using the catalyst system are disclosed.

8 Claims, No Drawings

CATALYST SYSTEM AND METHOD FOR REACTION OF OLEFIN

FIELD OF THE INVENTION

The present invention relates to a catalyst system, and a method for reaction of an olefin. More particularly, it relates to a novel catalyst system which can be preferably used in the trimerization, oligomerization or polymerization reaction of an olefin, and a method for the trimerization, oligomerization or polymerization reaction of an olefin, which comprises using the catalyst system.

BACKGROUND OF THE INVENTION

As a catalyst system which can be used in the trimerization, oligomerization or polymerization reaction of an olefin, a catalyst system comprising a metal source pyrrole-containing compound and a metal alkyl is known (see Japanese Patent Kokai (Laid-Open) No. 6-239920).

Under these circumstances, an object to be accomplished by the present invention is to provide a novel catalyst system which can be preferably used in the trimerization, oligomerization or polymerization reaction of an olefin, and a method for the trimerization, oligomerization or polymerization reaction of an olefin, which comprises using the catalyst system.

SUMMARY OF THE INVENTION

That is, the present invention relates to a catalyst system obtained by contacting the following components (A) to (C):

(A) a chromium compound,
(B) an imine compound, and
(C) a metal alkyl compound.

DETAILED DESCRIPTION OF THE INVENTION

The component (A) constituting the catalyst system of the present invention is a chromium compound represented by the general formula $CrX_1$ (wherein X represents an arbitrary organic or inorganic group or an electronegative atom; 1 represents an integer of 1 to 6; and each X of $X_1$ may be the same or different when 1 is not less than 2).

Examples of the organic group include hydrocarbon group having 1 to 30 carbon atoms, carbonyl group, alkoxy group, carboxyl group, β-diketonate group, β-ketocarboxyl group, β-ketoester group, amide group and the like. Examples of the hydrocarbon group include alkyl group, cycloalkyl group, aryl group, alkylaryl group, arylalkyl group, cyclopentadienyl group and the like. Examples of the inorganic group include nitric group, sulfuric group, cyano group and the like. Examples of the electronegative atom include halogen atom, oxygen atom and the like. Among them, an alkoxy, carboxyl, β-diketonate salt of chromium having a value of 2 to 4, a salt of β-ketoester and anion, and a chromium halide are preferred. Specific examples thereof include chromium (III) tris(2-ethylhexanoate), chromium (II) bis(2-ethylhexanoate), chromium (III) tris(naphthenate), chromium (II) bis(naphthenate), chromium (III) tris(acetate), chromium (II) bis(acetate), chromium (III) tris(acetylacetonate), chromium (II) bis(acetylacetonate), chromium (III) tris(2,2,6,6-tetramethyl-3,5-heptanedionate), chromium (IV) tetra(tert-butoxide), chromium (III) chloride, chromium (II) chloride, chromium (III) bromide, chromium (II) bromide, chromium. (III) fluoride, chromium (II) fluoride and the like.

A complex comprising the above chromium compound and an electron donor can be preferably used. The electron donor is selected from compounds containing nitrogen, oxygen, phosphorous or sulfur.

Examples of the nitrogen-containing compound include nitrile, amine, amide and the like. Specific examples thereof include acetonitrile, isopropylamine, n-butylamine, dimethylamine, diethylamine, di-n-propylamine, di-n-butylamine, ethylenediamine, pyridine, N,N-dimethylaminopyridine, picoline, lutidine, quinoline, isoquinoline, aniline, dimethylformamide, hexamethyldisilazane and the like.

Examples of the oxygen-containing compound include carboxylate, ether, ketone, alcohol, aldehyde and the like. Specific examples thereof include methyl acetate, ethyl acetate, tetrahydrofuran, dioxane, diethyl ether, dimethoxyethane, diglyme, triglyme, acetone, methyl ethyl ketone, methanol, ethanol, isopropanol, acetaldehyde, n-butylaldehyde and the like.

Examples of the phosphorous-containing compound include tributylphosphine, tributylphosphine oxide, triphenylphosphine, triphenylphosphine oxide, triethyl phosphate, triethyl phosphite, hexamethylphosphorous triamide and the like.

Examples of the sulfur-containing compound include carbon disulfide, thiophene, dimethyl sulfide, dimethyl sulfoxide, dimethyl sulfone and the like.

Accordingly, examples of the complex comprising a chromium compound and an electron donor include nitrile complex, amine complex, amide complex, ester complex, ether complex, ketone complex, alcohol complex, aldehyde complex, phosphine complex, thioether complex, etc. of chromium halide. Specific examples thereof include trichlorotris(ethylenediamine)chromium (III) 3.5 hydrate, trichlorotripyridine chromium (III), trichlorotri(4-ethylpyridine)chromium (III), trichlorotri(4-isopropylpyridine) chromium (III), trichlorotri(4-tert-butylpyridine)chromium (III), trichlorotri(4-phenylpyridine)chromium (III), trichlorotri(4-phenylpropylpyridine)chromium (III), trichloro(4-(5-nonyl)-pyridine) chromium (III), trichlorotri(3,5-lutidine) chromium (III), trichloroisoquinoline chromium (III), trichlorotrianiline chromium (III), trichlorotris(4-dimethylaminopyridine) chromium (III), tribromotripyridine chromium (III), trifluorotripyridine chromium (III), dichlorobispyridine chromium (II), dibromobispyridine chromium (II), trichlorotritetrahydrofuran chromium (III), dichlorodinitrosylbis(triphenylphosphine oxide)chromium, dichlorobis(triphenylphosphine oxide)chromium (II), dichlorodinitrobis(4-ethylpyridine)chromium, trichlorobis(tributylphosphine)chromium (II) dimer, trichloro(1,4,7-trimethy-1,4,7-triazacyclononane)chromium (III) and the like.

The compound (B) constituting the catalyst system of the present invention is an imine compound, that is, a compound having a double bond between carbon and nitrogen. Specific examples thereof include N-benzylideneaniline, N-benzylidenebenzylamine, N-benzylidenemethylamine, N-benzylidene-2-naphthylamine, N,N'-(1,2-ethanedylidene) biscyclohexylamine, glyoxalbis(diisopropylmethylimine), glyoxalbis(di-n-propylmethylimine), glyoxalbis (isobutylimine), glyoxalbis(heptylimine), glyoxalbis(1,1,3,3-tetramethylbutylimine), glyoxalbis(4-tert-butylcyclohexylimine), glyoxalbis(cyclododecylimine), glyoxalbis(adamantaneimine), glyoxalbis(tritylimine), glyoxalbis(phenylimine), glyoxalbis(2-methylphenylimine), glyoxalbis(2,6-dimethylphenylimine), glyoxalbis(4-methoxyphenylimine), methylglyoxalbis(2,6-dimethylphenylimine), diacetylbis(methylimine), diacetylbis(isopropylimine), diacetylbis(2-methylphenylimine), diacetylbis(2,6-dimethylphenylimine), diacetylbis(2,6-diisopropylphenylimine), 2,2'-bis(2-oxazoline), glyoxal dioxime, dimethyl glyoxime, glyoxalbis(2-hydroxyanil), glyoxaldithiosemicarbazone, N,N'-disalicylalethylenediamine, N,N'-disalicylal-1,2-propanediamine, N,N'-disalicylal-1,3-propanediamine, N,N'-disalicylal-1,4-butanediamine, N,N'-disalicylal-1,6-hexanediamine, acetone azine and compounds represented by the following formulas (B1) to (B5).

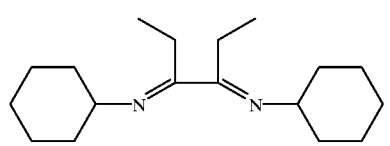

B1

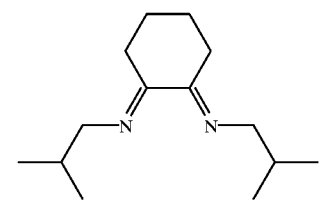

B2

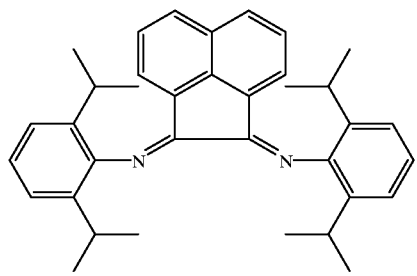

B3

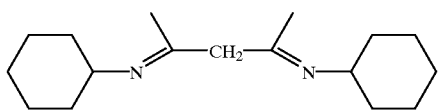

B4

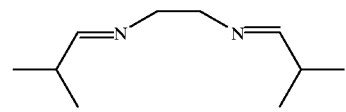

B5

As the component (B), a diimine compound represented by the following general formula (1) or (2) is preferred. An α-diimine compound represented by the general formula (1) wherein m is 0 is most preferred.

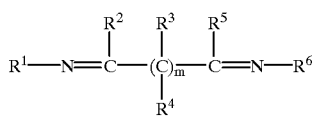

(1)

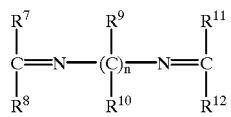

(2)

(wherein $R^1$ to $R^{12}$ represent a hydrogen atom or a hydrocarbon group, and the hydrocarbon group is an alkyl group having 1 to 30 carbon atoms, a cycloalkyl group having 3 to 30 carbon atoms, a cyclopentadienyl group having 5 to 30 carbon atoms, an aryl group having 6 to 30 carbon atoms, an alkylaryl group having 6 to 30 carbon atoms or an arylalkyl group having 6 to 30 carbon atoms. Furthermore, these groups may be groups containing a halogen atom, an oxygen atom, a nitrogen atom, a silicon atom or a sulfur atom. At least two of $R^1$ to $R^6$ and $R^1$ to $R^{12}$ may bond each other to form a ring. m and n represent an integer of 0 to 6).

Examples of an alkyl group include methyl group, ethyl group, n-propyl group, isopropyl group, n-butyl group, isobutyl group, tert-butyl group, pentyl group, hexyl group, diisopropylmethyl group, heptyl group, tetramethylbutyl group, octyl group and the like.

Examples of a cycloalkyl group include cyclohexyl group, tert-butylcyclohexyl group, cyclododecyl group, adamantyl group and the like.

Examples of a cyclopentadienyl group include cyclopentadienyl group, pentamethylcyclopentadienyl group and the like.

Examples of an aryl group, an alkylaryl group or an arylalkyl group include phenyl group, fluorophenyl group, trifluorophenyl group, pentafluorophenyl group, 2,6-dimethylphenyl group, 2,6-diisopropylphenyl group, acenaphthyl group and the like.

The component (C) constituting the catalyst system of the present invention is a metal alkyl compound. Examples of the metal alkyl compound include compound whose metal is aluminum, magnesium, lithium, boron or zinc.

Examples of the alkyl aluminum include trialkyl aluminum, alkyl aluminum hydride and the like. Specific examples of the trialkyl aluminum include trimethyl aluminum, triethyl aluminum, tri-n-propyl aluminum, tri-n-butyl aluminum, triisobutyl aluminum, tri-n-hexyl aluminum, tri-n-octyl aluminum and the like. Specific examples of the alkyl aluminum hydride include diethyl aluminum hydride, diisobutyl aluminum hydride. Specific examples of the alkyl magnesium include methyl magnesium chloride, methylmagnesium bromide, ethyl magnesium chloride, ethyl magnesium bromide, n-butylethyl magnesium, di-n-butyl magnesium, di-n-hexyl magnesium and the like. Specific examples of the alkyl lithium compound include methyl lithium, ethyl lithium, n-butyl lithium and the like. Specific examples of the alkyl boron compound include triethyl boron and the like. Specific examples of the alkyl zinc compound include dimethyl zinc, diethyl zinc and the like. Among them, an alkyl aluminum compound is preferred and a trialkyl aluminum is most preferred.

A ratio of the amount (molar ratio) of the components (A), (B) and (C) used is normally 1:(0.5–50):(1–500), preferably 1:(1–50):(5–100), more preferably 1:(1–30):(5–100). When the amount of the component (A) is too small, the activity is sometimes insufficient. When the amount of the component (B) is too small, the activity is sometimes insufficient. When the amount of the component (C) is too small, the activity is sometimes insufficient.

In the present invention, the trimerization, oligomerization or polymerization reaction of an olefin is conducted using a catalyst system obtained by contacting the above components (A) to (C). When a specific fourth component is used, in addition to the components (A) to (C), the catalytic activity and selectivity are further improved and, therefore, it is preferred. Examples of the fourth component include at least one compound of the compounds (D) to (G).

As one of the fourth component, a halogen-containing compound (D) is used. The halogen-containing compound may be any compound containing a halogen atom. Among them, a halogen-containing compound containing an element selected from the group 13 (IIIB) and a group 14 (IVB) of the periodic table is preferred. The halogen element may be fluorine, chlorine, bromine and iodine. Preferred are chlorine and bromine. The element of the group 13 (IIIB) may be boron, aluminum, gallium and indium. Preferred are boron and aluminum. The element of the group 14 (IVB) may be carbon, silicon, germanium and tin.

Examples of the halogen-containing compound include metal halogen compound, halogenated hydrocarbon and the like. Examples of the metal halogen compound include inorganic metal halogen compound and organometallic halogen compound. Examples of the halogenated hydrocarbon include halogenated chain hydrocarbon compound, halogenated cyclic hydrocarbon compound, halogenated aromatic hydrocarbon compound and the like.

Specific examples of the halogen-containing compound containing an element of the group 13 (IIIB) include boron trichloride, boron tribromide, aluminum trichloride, ethyl aluminum dichloride, diethyl aluminum chloride, ethyl aluminum sesquichloride, isobutyl aluminum dichloride, diisobutyl aluminum chloride, gallium trichloride and the like.

Specific examples of the halogen-containing compound containing an element of the group 14 (IVB) include carbon tetrachloride, chloroform, methylene chloride, methyl chloride, n-hexyl chloride, n-octyl chloride, benzene chloride, 1,4-dichlorobutane, 1,6-dichlorohexane, 1,1,2,2-tetrachloroethane, pentachlorocyclopropane, 1,2,3,4,5,6-hexachlorocyclohexane, ethyl bromide, n-butyl bromide, isobutyl bromide, tert-butyl bromide, n-hexyl bromide, n-octyl bromide, benzene bromide, 1,4-dibromobutane, 1,6-dibromohexane, hexafluorobenzene, silicon tetrachloride, dimethyldichlorosilane, chlorotrimethylsilane, germanium tetrachloride, tin tetrachloride, tin dichloride and the like.

As one of the fourth component, a phosphorous-containing compound (E) is used. Examples of the phosphorous-containing compound include phosphine compound, phosphine oxide compound, phosphorous acid ester compound, phosphonate compound, phosphinous acid ester compound, phosphinate compound, phosphate compound, phosphite compound and the like.

Specific examples of the phosphine compound include triphenylphosphine, trimethylphosphine, triethylphosphine, tributylphosphine, 1,2-bis(diphenylphosphino)ethane, 1,3-bis(diphenylphosphino)propane and the like.

Specific examples of the phosphine oxide include triphenylphosphine oxide, triethylphosphine oxide and the like.

Specific examples of the phosphonous acid ester compound include phenylphosphonous acid diethyl, methylphosphonous acid diphenyl and the like.

Specific examples of the phosphinous acid ester compound include diphenylphosphinous acid methyl, dibutylphosphinous acid ethyl and the like.

Specific examples of the phosphinate compound include methyl diethylphosphinate, methyl methylphosphinate and the like.

Specific examples of the phosphate compound include trimethyl phosphate, triethyl phosphate, tri-n-propyl phosphate, tri-n-butyl phosphate and the like.

Specific examples of the phosphite compound include trimethyl phosphite, triethyl phosphite, tri-n-propyl phosphite, tri-n-butyl phosphite and the like.

As one of the fourth component, a silicon-containing compound (F) is used. Specific examples thereof include tetramethoxysilane, tetraethoxysilane, tetraisopropoxysilane, tetra-n-butoxysilane, trimethoxy(methyl)silane, triethoxy(methyl)silane, dimethoxydimethylsilane, methoxytrimethylsilane, 1,1,1,3,3,3-hexamethyldisilazane, trimethylsilylacetamide, N,N-diethylaminotrimethylsilane, nonamethyltrisilazane and the like.

As one of the forth component, alcohols or phenols (G) are used.

As the alcohols, those having 1 to 20 carbon atoms are preferred. Specific examples thereof include methanol, ethanol, isopropanol, 2-ethylhexanol, hexafluoroisopropanol and the like.

As the phenols, those having 6 to 30 carbon atoms are preferred. Specific examples thereof include phenol, hydroquinone, resolcinol, catechol, bisphenol A, 2,4,6-tri-tert-butylphenol, 3-dimethylaminophenol, 3,4,5-trimethoxyphenol, 2,4,6-trichlorophenol and the like.

When using the components (D) to (G), the total amount of the components (D) to (G) per mol of the component (A) is preferably from 0.1 to 50 mol, more preferably from 0.5 to 30 mol.

The catalyst system of the present invention is a catalyst system obtained by contacting the above components (A) to (C) as an essential component, in addition to the components (D) to (G), if necessary. As a specific method of preparing a catalyst system, for example, there may be used a method of dissolving or suspending the respective components, which form the catalyst system, in a hydrocarbon or halogenated hydrocarbon solvent with stirring under atmosphere such as inert gas (e.g. nitrogen, argon, etc.) or ethylene. Examples of the solvent include propane, butane, isobutane, pentane, hexane, cyclohexane, 1-hexene, heptane, 1-octene, octane, toluene, xylene, chlorobenzene, dichlorobenzene and the like. These solvents may be used alone or in combination thereof.

The contact embodiment of the respective catalyst components is not specifically limited. Examples of the preferred contact embodiment include method of firstly mixing the component (A) with the component (B) and adding the component (C) to the resulting solution or suspension; method of firstly mixing the component (B) with the component (C) and adding the component (A) to the resulting solution or suspension; method of introducing the components (A), (B) and (C) in a reaction vessel, simultaneously and independently; method of introducing a solution or suspension obtained by contacting the component (A) with the component (B) in a reaction vessel, together with the component (C), independently; and method of introducing a solution or suspension obtained by contacting the component (B) with the component (C) in a reaction vessel, together with the component (A), independently.

When the compounds represented by (D), (E), (F) and (G) are expressed as the fourth component, examples of the contact embodiment of the respective catalyst components include method of firstly mixing the component (A) with the component (B), adding the component (C) to the resulting solution or suspension and further adding the fourth component to the solution or suspension; method of firstly mixing the component (A) with the component (B), adding the fourth component to the resulting solution or suspension and further adding the component (C) to the solution or suspension; method of firstly mixing the component (A) with the component (B) and adding a mixed solution of the component (C) and the fourth component to the resulting solution or suspension; method of firstly mixing the component (B) with the component (C), adding the component (A) to the resulting solution or suspension and further adding the fourth component to the solution or suspension; method of firstly mixing the component (B) with the component (C), adding the fourth component to the resulting solution or suspension and further adding the component (A) to the solution or suspension; method of firstly mixing the component (B) with the component (C) and adding a mixed solution of the component (A) and the fourth component to the resulting solution or suspension; method of firstly mixing the component (A) with the fourth component, adding the component (B) to the resulting solution or suspension and further adding the component (C) to the solution or suspension; method of introducing the components (A), (B) and (C) and the fourth component in a reaction vessel, simultaneously and independently; method of introducing a solution or suspension obtained by contacting the component (A) with the component (B) in a reaction vessel, together with the component (C) and the fourth component, independently; method of introducing a solution or suspension obtained by contacting the component (A) with the component (B) in a reaction vessel, together with a mixed solution of the component (C) and the fourth component, independently; method of introducing a solution or suspension obtained by contacting the component (A) with the fourth component in a reaction vessel, together with the components (B) and (C), independently; method of introducing a solution or suspension obtained by contacting the component (B) with the component (C) in a reaction vessel, together with the component (A) and fourth component, independently; and method of introducing a solution or suspension obtained by contacting the component (B) with the component (C) in a reaction vessel, together with a mixed solution of the component (A) and fourth component, independently.

The contact embodiment of the respective catalyst components and α-olefin is not specifically limited. Examples of the preferred contact embodiment include method of introducing α-olefin in a catalyst system obtained by contacting the components (A) to (C); method of introducing the component (C) and α-olefin in a solution or suspension obtained by contacting the component (A) with the component (B); method of introducing the component (A) and α-olefin in a solution or suspension obtained by contacting the components (B) and (C); method of introducing the components (A), (B) and (C) and α-olefin, simultaneously and independently; method of introducing a catalyst system obtained by contacting the components (A) to (C) in a reaction vessel, together with α-olefin, independently; method of introducing a solution or suspension obtained by contacting the component (A) with the component (B) in a reaction vessel, together with the component (C) and α-olefin, independently; and method of introducing a solution or suspension obtained by contacting the component (B) with the component (C) in a reaction vessel, together with the component (A) and α-olefin, independently.

When the compounds represented by (D), (E), (F) and (G) are expressed as the fourth component, examples of the contact embodiment of the respective catalyst components and α-olefin include method of introducing α-olefin in a catalyst system obtained by contacting the components (A) to (C) and the fourth component; method of introducing the fourth component and α-olefin in a catalyst system obtained by contacting the components (A) to (C); method of introducing the component (C) and α-olefin in a catalyst system obtained by contacting the components (A) and (B) and the fourth component; method of introducing the component (A) and α-olefin in a solution or suspension obtained by contacting the components (B) and (C) and the fourth component; method of introducing a solution or suspension obtained by contacting the component (C) with the fourth component, together with α-olefin, in a solution or suspension obtained by contacting the component (A) with the component (B); method of introducing a solution or suspension obtained by contacting the component (B) with the component (C), together with α-olefin, in a solution or suspension obtained by contacting the component (A) with the fourth component; method of introducing the components (A), (B) and (C), the fourth component and α-olefin in a reaction vessel, simultaneously and independently; method of introducing a solution or suspension obtained by contacting the components (A) to (C), together with the fourth component and α-olefin, in a reaction vessel, independently; method of introducing a solution or suspension obtained by contacting the components (A) and (B) and the fourth component in a reaction vessel, together with the component (C) and α-olefin, independently; method of introducing a solution or suspension obtained by contacting the components (B) and (C) and the fourth component, together with the component (A) and α-olefin, in a reaction vessel, independently; method of introducing a solution or suspension obtained by contacting the component (A) with the component (B), together with a solution or suspension obtained by contacting the component (C) with the fourth component, and α-olefin, in a reaction vessel, independently; and method of introducing a solution or suspension obtained by contacting the component (A) with the fourth component in a reaction vessel, together with a solution or suspension obtained by contacting the component (B) with the component (C), and α-olefin, independently.

It should be avoided to firstly contact the component (A) with the component (C) in view of obtaining sufficiently high catalytic activity.

A contact temperature of the respective components is normally from −50 to 150° C. and a contact time is normally from 1 second to 48 hours.

The resulting catalyst system can also be fed to the reaction after removing the solvent, but can be fed to the reaction as it is without removing the solvent. It may also be used as a supporting catalyst prepared from an inorganic carrier (e.g. silica, alumina, silica-alumina, zeolite, aluminum phosphate, clay mineral, etc.) and an organic carrier (e.g. ion-exchange resin, polystyrene, polyvinyl pyridine, etc) which support the catalyst system.

The catalyst system of the present invention can be used in the trimerization, oligomerization or polymerization reaction of an olefin. Examples of the olefin used in the present invention include ethylene, propylene, 1-butene, 2-butene, isobutene, 1-hexene, styrene and a mixture thereof. Among them, α-olefin, particularly ethylene, is preferred. The trimerization, oligomerization or polymerization reaction of an olefin can be conducted by the solution reaction or slurry reaction in the presence of a solvent such as propane, butane, isobutane, pentane, hexane, cyclohexane, 1-hexene, heptane, 1-octene, octane, toluene, xylene, chlorobenzene, dichlorobenzene, etc., or liquid phase reaction or vapor phase reaction in the absence of the solvent. A reaction temperature is normally from 0 to 300° C., preferably from 0 to 200° C. reaction pressure is normally from atmospheric pressure to 200 kg/cm$^2$, preferably from 10 to 100 kg/cm$^2$.

The catalyst of the present invention can be preferably used in the reaction for the production of 1-hexene by trimerizing ethylene. As the embodiment of the method using the catalyst system of the present invention, a method of producing 1-hexene by trimerizing ethylene will be explained.

The reaction may be conducted by charging catalyst components of the present invention and a solvent in a pressure reaction vessel, introducing ethylene, followed by heating. An amount of the catalyst system used is set so that a concentration of a chromium atom in the reaction solution is preferably within the range from 0.000001 to 0.5 mol/l, more preferably from 0.00001 to 0.1 mol/l. When the amount of the catalyst system used is too small, the activity is sometimes insufficient. A reaction temperature is normally from 0 to 200° C., preferably from 0 to 150° C. When the reaction temperature is too low, the activity may be low. On the other hand, when the reaction temperature is too high, the selectivity of 1-hexene as a desired product sometimes becomes low. A reaction pressure is normally from atmospheric pressure to 200 kg/cm$^2$, preferably from 10 to 100 kg/cm$_2$. When the reaction pressure is too low, the activity is sometimes insufficient. A reaction time is normally from 0.1 to 8 hours, preferably from 0.5 to 7 hours. When the reaction time is too short, the reactivity sometimes becomes short. In order to separate and recover 1-hexene as the desired product from the reaction mixture in the present invention, for example, a method such as distillation can be used. In order to separate the catalyst component and/or polymer as by-products from the reaction mixture in the present invention, there may be used a known method (see Japanese Patent Kokai (Laid-Open) Nos. 7-149671, 7-149674, 7-149677, 8-239419, 8-245429, 8-245430, 8-245431, 8-283330 and 8-295705).

As described above, according to the present invention, there could be provided a novel catalyst system which can be preferably used in the trimerization, oligomerization or polymerization reaction of an olefin, and a method for the trimerization, oligomerization or polymerization reaction of an olefin, which comprises using the catalyst system.

The following Examples further illustrate the present invention in detail but are not to be construed to limit the scope thereof.

EXAMPLE 1

Synthesis of glyoxalbis(1,1,3,3,-tetramethylbutylimine 1,1,3,3-tetramethylbutylamine (12.95 g, 100 mmol) was charged in a reaction vessel replaced by nitrogen and dissolved in 100 ml of diethyl ether. This solution was cooled in an ice-water bath and glyoxal (7.26 g, 50.0 mmol) (40% by weight of an aqueous solution) was slowly added dropwise with stirring. After the completion of the dropwise addition, the reaction solution was continuously stirred for 2 hours with cooling in an ice-water bath. After the aqueous layer was separated, the organic layer was washed with water, dried and concentrated to obtain a solid crude product. This solid crude product was recrystallized from acetonitrile to obtain a colorless solid. On the basis of 1H NMR, this colorless solid was identified as glyoxalbis(1,1,3,3-tetramethylbutylimine) represented by the following structural formula.

1H NMR (CDCl$_3$, 400 MHz) 0.92 (s, 18H), 1.29 (s, 12H), 1.60 (s, 4H), 7.94 (s, 2H)

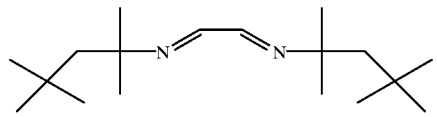

Ethylene trimerization reaction

Under argon atmosphere, in a pressure reaction vessel (inner volume: 0.2 l) cooled in an ice-water bath, glyoxalbis (1,1,3,3-tetramethylbutylimine) (B) (0.0280 g, 0.10 mmol) and triethyl aluminum (C) (0.0594 g, 0.52 mmol) (1.05 mol/l of a heptane solution) were dissolved in 80 ml of heptane which was previously deaerated and dehydrated. To this solution, chromium (III) tris(2-ethylhexanoate) (A) (0.00318 g, 0.0066 mmol) (heptane solution having a chromium concentration of 0.94% by weight) and 40 ml of heptane were added, followed by stirring for 20 minutes. Then, ethylene was introduced at a pressure of 20 kg/cm$^2$G. Furthermore, the trimerization reaction was conducted by heating with stirring. Incidentally, the reaction was conducted under the conditions of a reaction temperature of 120° C., a reaction pressure of 40 kg/cm$^2$G and a reaction time of 1.5 hours, and ethylene was fed in response to a demand during the reaction. After 1.5 hours, the reaction solution was ice-cooled and the reaction mixture was recovered, followed by solid-liquid separation. An amount of a polymer produced was determined from a weight of the solid. The aqueous phase was analyzed by gas chromatography and an amount of the product was determined. The conditions and results are shown in Table 1.

EXAMPLE 2

According to the same manner as that described in Example 1 except for changing the amount of (A) to 0.0120 g (0.025 mmol), the reaction was conducted. The conditions and results are shown in Table 1.

EXAMPLE 3

According to the same manner as that described in Example 1 except for adding n-butyl bromide (D) (0.00145 g, 0.0106 mmol) (6.4% by weight of a heptane solution) before adding (A), the reaction was conducted. The conditions and results are shown in Table 1.

EXAMPLE 4

According to the same manner as that described in Example 1 except for adding 1, 2-diphenylphosphinoethane (E1) (0.0199 g, 0.0499mmol) before adding (A), the reaction was conducted. The conditions and results are shown in Table 1.

EXAMPLE 5

According to the same manner as that described in Example 2 except for adding triethyl phosphite (E2) (0.0112 g, 0.0948 mmol) immediately after adding (A), the reaction was conducted. The conditions and results are shown in Table 2.

EXAMPLE 6

According to the same manner as that described in Example 2 except for adding tetraethoxysilane (F) (0.0160 g, 0.0768 mmol) immediately after adding (A), the reaction was conducted. The conditions and results are shown in Table 2.

EXAMPLE 7

According to the same manner as that described in Example 2 except for adding bisphenol A (G) (0.0178 g,

TABLE 1

|  | Ex. 1 | Ex. 2 | Ex. 3 | Ex. 4 |
|---|---|---|---|---|
| Catalyst component *1 | | | | |
| (A) | 1 | 1 | 1 | 1 |
| (B) | 15 | 4 | 15 | 15 |
| (C) | 79 | 20 | 78 | 78 |
| (D) |  |  |  | 1.6 |
| (E-1) |  |  |  | 7.5 |
| Results *2 | | | | |
| Activity *3 | 22995 | 10629 | 16849 | 17186 |
| Selectivity % *4 | | | | |
| $C_4$ Compounds | 12.2 | 9.6 | 2.0 | 8.1 |
| $C_6$ Compounds | 72.4 | 74.3 | 81.6 | 77.0 |
| $C_8$ Compounds | 1.5 | 2.3 | 1.0 | 1.3 |
| $C_{10}$ Compounds | 9.4 | 10.3 | 11.1 | 10.2 |
| Polymer | 3.0 | 1.3 | 2.2 | 1.6 |
| Purity of 1-hexene *5 | 80.5 | 79.2 | 79.8 | 80.4 |

TABLE 2

|  | Ex. 5 | Ex. 6 | Ex. 7 |
|---|---|---|---|
| Catalyst component *1 | | | |
| (A) | 1 | 1 | 1 |
| (B) | 4 | 4 | 4 |
| (C) | 20 | 19 | 20 |
| (E-2) | 3.7 | | |
| (F) |  | 2.8 | |
| (G) |  |  | 3.0 |
| Results *2 | | | |
| Activity *3 | 11788 | 10409 | 12088 |
| Selectivity % *4 | | | |
| $C_4$ Compounds | 8.6 | 6.6 | 10.0 |
| $C_6$ Compounds | 77.1 | 77.9 | 74.6 |
| $C_8$ Compounds | 1.4 | 1.4 | 1.9 |
| $C_{10}$ Compounds | 10.0 | 11.0 | 110.1 |
| Polymer | 0.8 | 0.6 | 1.1 |
| Purity of 1-hexene *5 | 80.0 | 79.8 | 79.4 |

*1 Catalyst component
A: Chromium (III) tris(2-ethylhexanoate)
B: Glyoxalbis (1,1,3,3-tetramethylbutylimine)
C: Triethyl aluminum
D: n-Butyl bromide
E1: 1,2-Bis (diphenylphosphino)ethane
E2: Triethyl phosphite
F: Tetraethoxysilane
G: Bisphenol A
The numerical values in the tables represent an amount to be used (mol) per mol of the component (A).
*2 Results under the following reaction conditions
Reaction temperature: 120° C.
Reaction pressure: 40 kg/cm²G
Reaction time: 1.5 hours
*3 Activity: total amount (g) of product per g of chromium atom as catalyst per unit time [g-total amount of product/g-chromium atom/hour]
*4 Selectivity
$C_4$ compounds: produced $C_4$ compounds/total amount of product (g) × 100
$C_6$ compounds: produced $C_6$ compounds/total amount of product (g) × 100
$C_8$ compounds: produced $C_8$ compounds/total amount of product (g) × 100
$C_{10}$ compounds: produced $C_{10}$ compounds/total amount of product (g) × 100
*5 purity of 1-hexene: produced 1-hexene (g)/produced $C_6$ compound (g) × 100

What is claimed is:

1. A catalyst system obtained by contacting the following components (A) to (C):

(A) a chromium compound, (B) an imine compound having a double bond between carbon and nitrogen, wherein the component (B) is a diimine compound represented by the following general formulae (1) or (2):

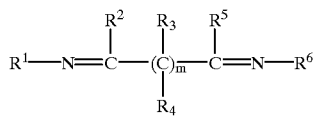

(1)

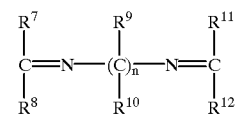

(2)

wherein $R^1$ to $R^{12}$ represent a hydrogen atom or a hydrocarbon group, and the hydrocarbon group is an alkyl group having 1 to 30 carbon atoms, a cycloalkyl group having 3 to 30 carbon atoms, a cyclopentadienyl group having 5 to 30 carbon atoms, an aryl group having 6 to 30 carbon atoms, an alkylaryl group having 6 to 30 carbon atoms or an arylalkyl group having 6 to 30 carbon atoms and these groups may be groups containing a halogen atom, an oxygen atom, a nitrogen atom, a silicon atom, or a sulfur atom: at last two of $R^1$ to $R^6$ and $R^7$ to $R^{12}$ may bond to each other to form a ring: and m and n represent an integer of 0 to 6, and (C) a metal alkyl compound.

2. The catalyst system according to claim 1, wherein the component (B) is represented by the general formula (1) of claim 2 and m is 0.

3. The catalyst system according to claim 1, wherein the metal of the component (C) is aluminum, magnesium, lithium, boron or zinc.

4. The catalyst system according to claim 1, wherein the component (C) is an alkyl aluminum compound.

5. The catalyst system according to claim 1, wherein the component (C) is a trialkyl aluminum compound.

6. The catalyst system according to claim 1, wherein a ratio of the amount (molar ratio) of the components (A), (B) and (C) used is 1:0.5–50:1–500.

7. The catalyst system according to claim 1, which is obtained by contacting at least one of the following components (D) to (G):

(D) a halogen-containing compound, (E) a phosphorous-containing compound, (F) a silicon-containing compound, and (G) an alcohol or a phenol, in addition to the components (A) to (C) of claim 1.

8. The catalyst system according to claim 7, wherein the total amount of the components (D) to (G) per mol of the component (A) is from 0.1 to 50 mol.

* * * * *